United States Patent [19]

You et al.

[11] Patent Number: 5,473,247
[45] Date of Patent: Dec. 5, 1995

[54] APPARATUS FOR DISCRIMINATING DEFECTS IN TOP AND BOTTOM SURFACES OF OBJECTS

[75] Inventors: Zhongging You, Port Chester; Robert A. Brooks, White Plains; Richard Colman, Carmel; Paul J. Bebick, Bronx, all of N.Y.

[73] Assignee: Magnetic Analysis Corporation, Mt. Vernon, N.Y.

[21] Appl. No.: 43,181

[22] Filed: Apr. 6, 1993

[51] Int. Cl.⁶ .......................... G01N 27/82; G01N 27/90; G01R 33/12
[52] U.S. Cl. .......................... 324/227; 324/232; 324/240; 324/262
[58] Field of Search .......................... 324/220, 221, 324/227, 228, 230, 239–243, 262, 232

[56] References Cited

U.S. PATENT DOCUMENTS

| | | | |
|---|---|---|---|
| 3,343,079 | 9/1967 | Crouch | 324/227 |
| 3,538,433 | 11/1970 | Wood et al. | 324/227 |
| 3,940,689 | 2/1976 | Johnson, Jr. | 324/221 |
| 4,445,088 | 4/1984 | Schubel | 324/240 |
| 4,602,212 | 7/1986 | Hiroshima et al. | 324/227 |
| 4,751,460 | 1/1988 | Mato, Jr. | 324/221 |
| 4,878,180 | 10/1989 | McWhirter et al. | 324/220 |
| 4,992,735 | 2/1991 | Cullen et al. | 324/220 |

Primary Examiner—Sandra L. O'Shea
Assistant Examiner—Jay M. Patidar
Attorney, Agent, or Firm—Robin, Blecker, Daley & Driscoll

[57] ABSTRACT

Apparatus for non-destructive examination of a plate for defects existing in one of both of opposed first and second surfaces thereof includes a rotatable support platform, an eddy current coil structure for inducing eddy currrents in the plate located at a first location in the platform, a first magnetic flux generator disposed at a second location in the platform, the second location being opposite the first location on a line extending from the first location through the platform center. A drive unit rotates the platform relative to the plate.

7 Claims, 6 Drawing Sheets

APPARATUS FOR DISCRIMINATING DEFECTS IN TOP AND BOTTOM SURFACES OF OBJECTS

FIELD OF THE INVENTION

This invention relates generally to examination of plate members for flaws therein and pertains more particularly to system and apparatus for magnetic field testing of tank bottoms.

BACKGROUND OF THE INVENTION

Large oil tanks may sit on the ground for thirty to fifty years or more. Due to various conditions and environmental factors, the bottom of the tank can become seriously corroded on its interior or top surface or on its back or ground-contacting surface. Where the corrosion gives rise to leakage of contents of the tank, evidently drastic environmental problems can occur.

Governmental regulations in place at present require regular inspections of the tank bottom to predict the remaining life thereof and to spot the locations where a proper repair or replacement is needed. Top surface conditions can be visually examined if the surface is not coated. But, the more prevalent back surface corrosion is both more serious and more difficult to detect and locate.

Two currently used inspection methods used to detect and locate back surface corrosion are based in the techniques of ultrasonics and flux leakage.

The ultrasonics method can be used to measure plate thickness and therefore detect plate thinning due to back surface corrosion. However, the technique is usually slow and tedious to apply in a sweeping inspection, due to the need for an oil or water based medium between the transducer and the plate under inspection. For a tank of one hundred and eighty feet in diameter, inspection time can run as much as five weeks for the completion of a track-mounted ultrasonic inspection. Further, the effectiveness of this practice is called into serious doubt if the tank bottom has its top surface sealed with a laminate or coating which has become delaminated or disbonded from the top surface. Thus, under such conditions, the ultrasonic pulse will not properly propagate into the plate, severely degrading the inspection capability. Accordingly, the ultrasonic method is generally more useful in determining the remaining plate thickness after an area of corrosion has previously been identified by the more easily and rapidly applied flux leakage method, which requires no liquid couplant and can inspect a tank of the noted size in about five days.

Extolling of the flux leakage method, however, cannot be such as to identify it as a problem-free practice. One of the major problems associated with the use of the flux leakage method is its inability to discern differences between top surface and back surface corrosion signal indications. Signals arising from top surface conditions can be greater in amplitude than back surface corrosion-indicating signals and the frequencies of the respective signals are virtually indiscernible.

Given the present state of flux leakage art, as above discussed, it has been almost impossible to this time to identify back surface corrosion as such in a significant percentage of tank bottoms while in the presence of extensive top surface corrosion.

From applicants' perspective, current flux leakage technology in plate inspection, and particularly in the inspection of tank bottoms, is lacking fundamentally in its inability to distinguish corrosion on one plate surface from that on an opposite plate surface, e.g., on a tank bottom top surface and on a tank bottom back surface. None of the known full magnetic saturation types of flux leakage systems, i.e., using either a coil type or a Hall element type leakage flux sensor, has the capacity for such distinction.

SUMMARY OF THE INVENTION

The present invention has as its primary object the provision of systems and apparatus for improving the state of the art of plate inspection.

A more specific object of the invention is to provide the art with facility for discrimination as between top surface corrosion and back surface corrosion in the bottoms of tanks.

In attaining these and other objects, the invention provides systems and apparatus for identification of the source, one surface or an opposite surface of a plate, of corrosion or other defect. Probe apparatus is likewise provided for attaining these objects.

In accordance with the invention, steps for non-destructive examination of a plate for defects existing in one or both of opposed first and second surfaces thereof comprise concurrently examining plate locations with diverse examination techniques and comparing the respective detection results of such examination techniques for discriminating as between defects resident in the opposed surfaces of the plate.

More particularly, applicants employ one examination technique which provides output indications of defects in both surfaces and another examination technique which provides output indications of defects only in the readily accessible of the surfaces, e.g., in the case of a tank bottom, the top surface of the tank bottom.

As respects the attainment of the above-noted more specific object of the invention, applicants provide a system for non-destructive examination of a plate for defects existing in one or both of opposed first and second surfaces thereof, the system comprising generator means for providing a signal for use in inducing eddy currents in at least the first specimen surface and for providing a current supply for establishing a magnetic field in the specimen, detector means for detecting characteristics of eddy currents in the specimen and for detecting characteristics of magnetic flux leakage from the specimen, drive means for effecting relative movement between the specimen and the detector means to provide for examination of the specimen at multiple specimen locations and synchronous display means for joint display of the detected characteristics of the eddy currents in the specimen and of the detected characteristics of magnetic flux leakage from the specimen at each of the multiple specimen locations.

The detector means provides first and second output signals respectively indicative of the detected characteristics of the eddy currents in the specimen and of the detected characteristics of magnetic flux leakage from the specimen at each of the multiple specimen locations, the system further including first and second circuit means for respective separate processing of the first and second output signals, the first and second circuit means providing processed signals to the display means.

The generator means includes a high frequency oscillator for the inducing of eddy currents in the specimen and includes a direct current supply for the establishing of the magnetic field in the specimen.

The detector means includes probe apparatus comprising a platform supported for rotation relative to the specimen and the system includes a speed control and display synchronizing unit for controlling the rotational speed of the probe apparatus platform and effecting synchronous display of the processed signals provided by the first and second circuit means. The control unit preferably directs a fixed rotational speed for the probe apparatus platform, in which case, filtering characteristics are fixedly set for the fixed rotational speed. The control unit derives a single input from the probe apparatus platform per revolution thereof at the fixed speed and accordingly synchronizes the display unit based on the single per revolution input to display the processed signals provided by the first and second circuit means in synchronism.

On the other hand, the invention contemplates that the control unit may set the rotational speed of the probe apparatus platform to be variably settable, in which case, the control unit provides for filtering characteristics correspondingly with the variably set speed and furnishes the rotational speed per revolution indication to the display for synchronous presentation of the information.

The probe apparatus further includes first sensor means for receiving the generator means signal for inducing eddy currents in the specimen and thereby inducing eddy currents therein and for sensing eddy currents in the specimen and second sensor means for sensing flux leakage from the specimen, the first and second sensor means being fixedly supported by the probe apparatus platform to rotate therewith. The first sensor means includes first and second coils differentially connected to one another and the second sensor means includes at least one coil. The probe apparatus further includes a core member having end courses extending into proximity with the specimen and an intermediate course disposed interiorly of the second sensor means coil.

Further, the probe apparatus includes first and second electromagnets, excited respectively oppositely by the generator means current supply, and associated pole pieces, rendered respectively as north and south poles by the electromagnets for establishing flux in the specimen.

A slip ring unit has connection to the probe apparatus, the generator means and the first and second circuit means.

The foregoing and other objects and features of the invention will be further understood from the following detailed description of a preferred embodiment thereof and from the drawings, wherein like reference numerals identify like components throughout.

DETAILED DESCRIPTION OF THE PREFERRED EMBODIMENTS AND PRACTICES

Figure 1:
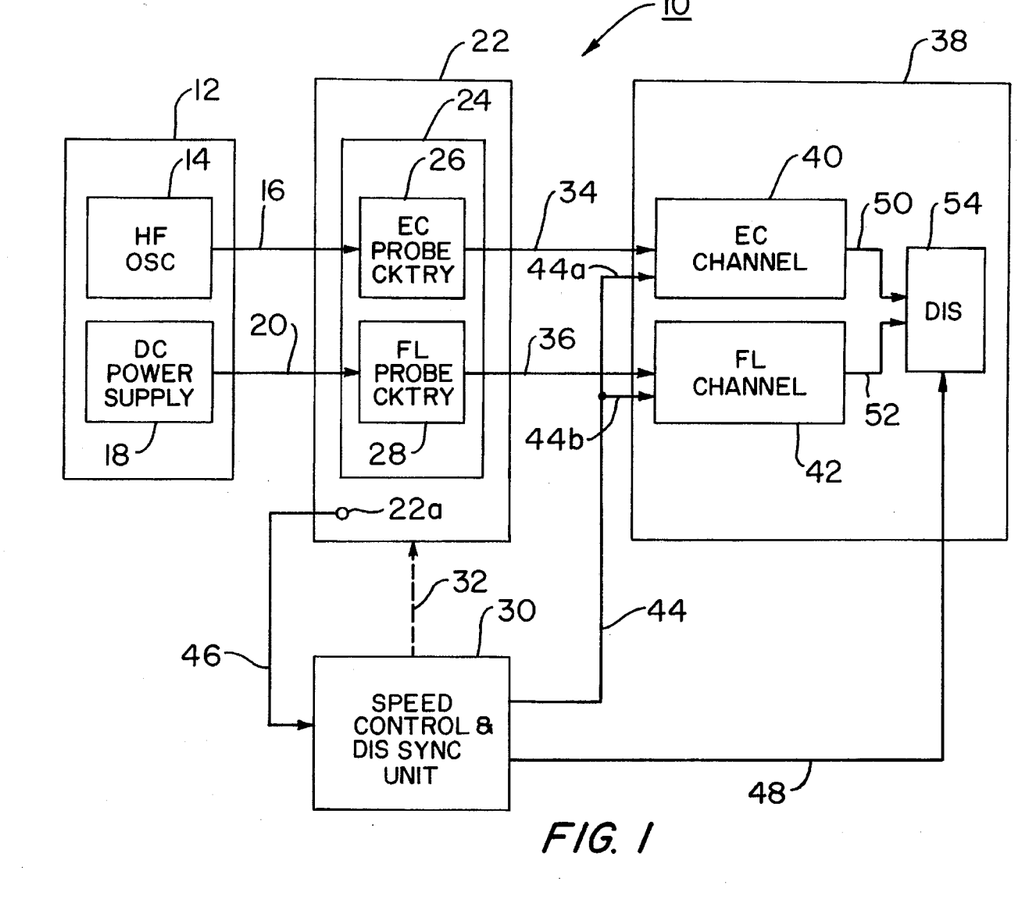
FIG. 1 is a functional block diagram of a system in accordance with the invention.

Referring to FIG. 1, system 10 includes a generator 12 which has a high frequency oscillator (HF OSC) 14, for providing on output line 16 eddy current drive signals, typically in the kilohertz range, and a direct current power supply (DC POWER SUPPLY) 18, for providing on output line 20 constant current for flux leakage driving through electromagnets below discussed.

Rotation platform 22 of FIG. 1 supports probe apparatus 24, which includes probe circuitry comprising eddy current probe circuitry (EC PROBE CKTRY) 26 and flux leakage probe circuitry (FL PROBE CKTRY) 28 and the electromagnets. As is discussed below in connection with FIG. 7 and the mobile test apparatus thereof, rotation platform 22 is supported for rotation relative to specimens being evaluated. The FIG. 1 system includes a speed control and display synchronizing unit (SPEED CONTROL & DIS SYNC UNIT) 30 and broken line 32 indicates mechanical rotational input to platform 22.

Outputs signals of circuitry 26 and circuitry 28 are applied respectively to lines 34 and 36 for conveyance to signal processing and display unit 38. Unit 38 includes an eddy current channel (EC CHANNEL) 40 connected to line 34 and a flux leakage channel (FL CHANNEL) 42 connected to line 36. Present speed rotational information is fed over lines 44, 44a and 44b to channels 40 and 42, which provide respective outputs over lines 50 and 52 to display (DIS) 54.

In present preferred contemplation of test apparatus, applicants would implement unit 30 for single speed, fixed rotation of platform 22, but contemplate apparatus in which the speed of rotation may be variably set. Platform 22 includes a sensor 22a at a fixed location thereon which issues a synchronizing output signal over line 46 to control unit 30 once per rotation of platform 22. In addition to the present speed rotational information on lines 44, 44a and 44b, unit 30 is responsive to the sensor 22a output signal on line 46 to provide a pulse on line 48 to display 54 for purposes below discussed.

Figure 2:
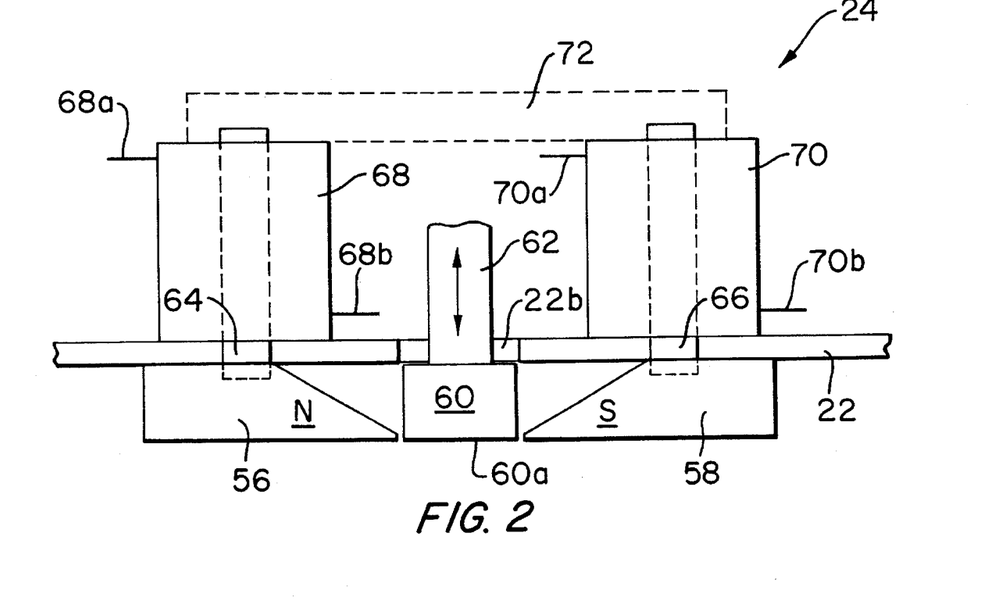
FIG. 2 is a schematic front elevation of probe apparatus 24 of the FIG. 1 system.
Figure 3:
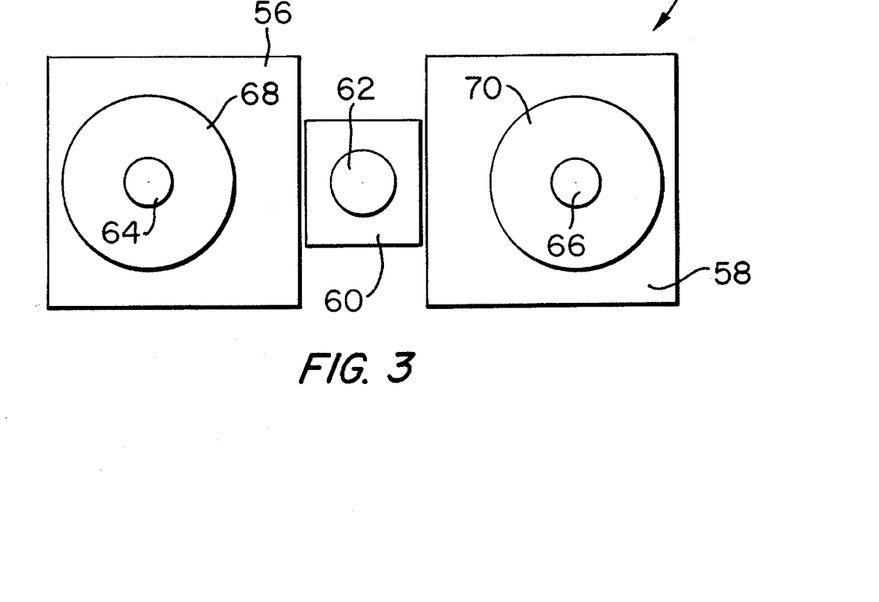
FIG. 3 is a plan view of the probe apparatus of FIG. 2, with rotation platform 22 omitted from the showing.

Turning to FIGS. 2 and 3, probe apparatus 24 includes pole pieces 56 and 58, between which is disposed probe 60. The probe is supported by shaft member 62 and input/output conductors of the probe are connected to a slip ring unit, below discussed. Shaft member 62 is movable as indicated by the double-arrow head toward and away from a specimen to be evaluated, through a passage 22b in platform 22.

Cores 64 and 66 are seated in the upper surfaces of pole pieces 56 and 58 and windings 68 and 70 circumscribe the cores. Conductors 68a, 68b and 70a, 70b communicate with the windings for excitation thereof.

A magnetic circuit is defined by core 64, pole piece 56, the specimen being evaluated, pole piece 58 and core 66 and is closed by a bridge member 72, shown in phantom in FIG. 2 as receiving ends of cores 64 and 66. Excitation of windings 68 and 70, which form electromagnets with their cores, gives rise to magnetic flux in the specimen.

Figure 4:
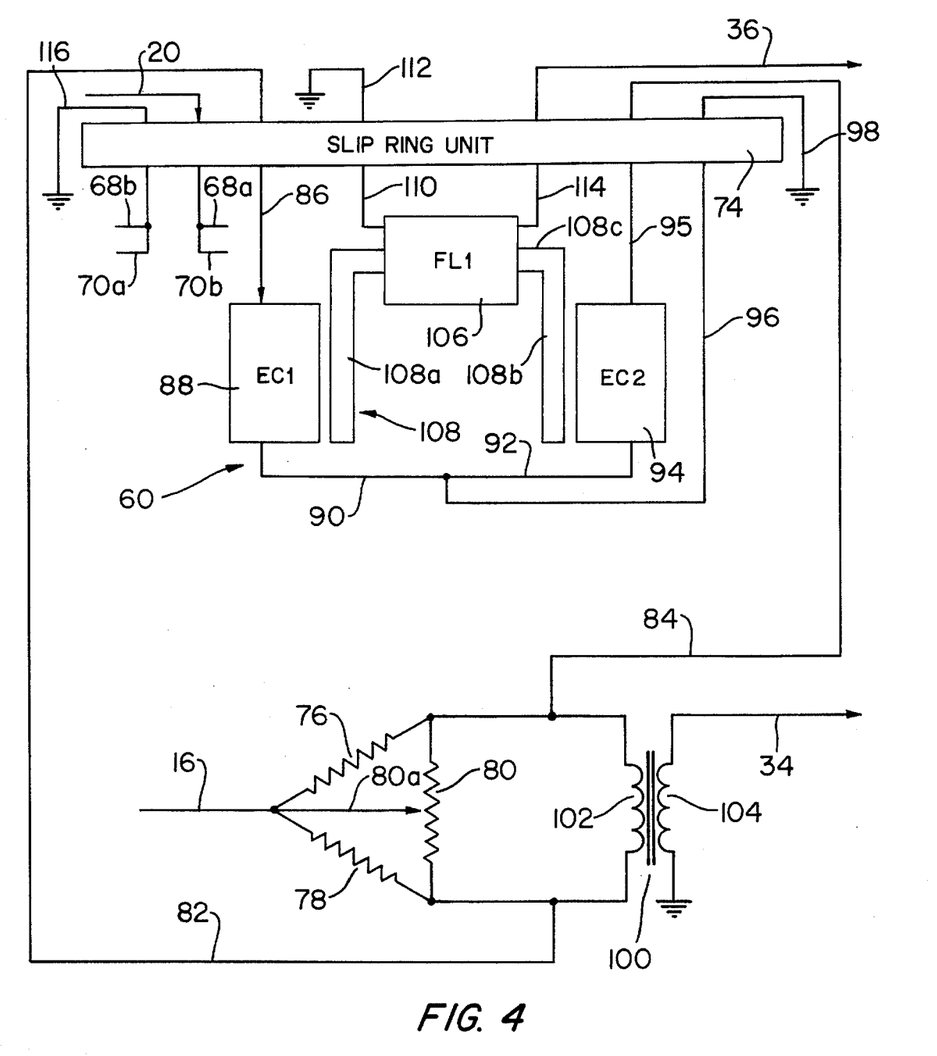
FIG. 4 is an electrical schematic diagram of EC probe circuitry 26 and LF probe circuitry 28 of the FIG. 1 system.

Referring now to FIG. 4, probe 60 of FIG. 2 and probe circuitries 26 and 28 of FIG. 1 will be further explained. The above-referenced SLIP RING UNIT is indicated at 74 and is operative to mate non-rotated components, e.g., oscillator 14 and power supply 18 of the FIG. 1 system, with the rotated probe apparatus components.

Line 16 is connected to a Wheatstone bridge arrangement, including resistors 76 and 78 ends of which are bridged by balancing potentiometer 80. Lines 82 and 84 connect resistors 76 and 78 to slip ring unit 74. Unit 74 output line 86 connects to a first eddy current coil (EC1) 88, the output of which is connected by line 90 and line 92 to second eddy current coil (EC2) 94, the output of which is connected by line 95 through unit 74 to line 84. The Wheatstone bridge is completed by line 96, unit 74 and grounded line 98, whereby the junction of coils 88 and 94 is grounded.

Potentiometer 80 has its wiper 80a adjusted to provide a null condition with a test (faultless) specimen in place. Under such null condition, the primary winding 102 of transformer 100 sees no input voltage variation and the secondary winding 104 sees no change and eddy current probe circuitry output line 34 so indicates.

High permeability member 108 of FIG. 4 has leg courses 108a and 108b extending to the specimen interface and central course 108c thereof serves as a core for flux leakage sensing coil (FL1) 106. One end of coil 106 is connected by line 110, slip ring unit 74 and line 112 to ground. The other end 114 of coil 106 is connected through line 114 and slip ring unit 74 to flux leakage probe circuitry output line 36.

Slip ring unit 74 further functions to connect the leakage flux (constant current) drive output line 20 of FIG. 1 to lines 68a and 70b, i.e., input lines to coils 68 and 70. The output lines of the coils, lines 68b and 70a, are grounded through unit 74 and grounded line 116. Based on their opposite current excitation, coils 68 and 70 effect respective north N and south S magnetic poles in pole pieces 56 and 58 (FIG. 2).

Eddy currents are induced in the specimen to be evaluated by coils 88 and 94, as excited from line 16 through unit 74. Eddy current permutations (modulation content) indicative of fault conditions are sensed and provided by signals on line 34. Flux leakage permutations indicative of fault conditions are sensed and indicated by signals on line 36.

Figure 5:
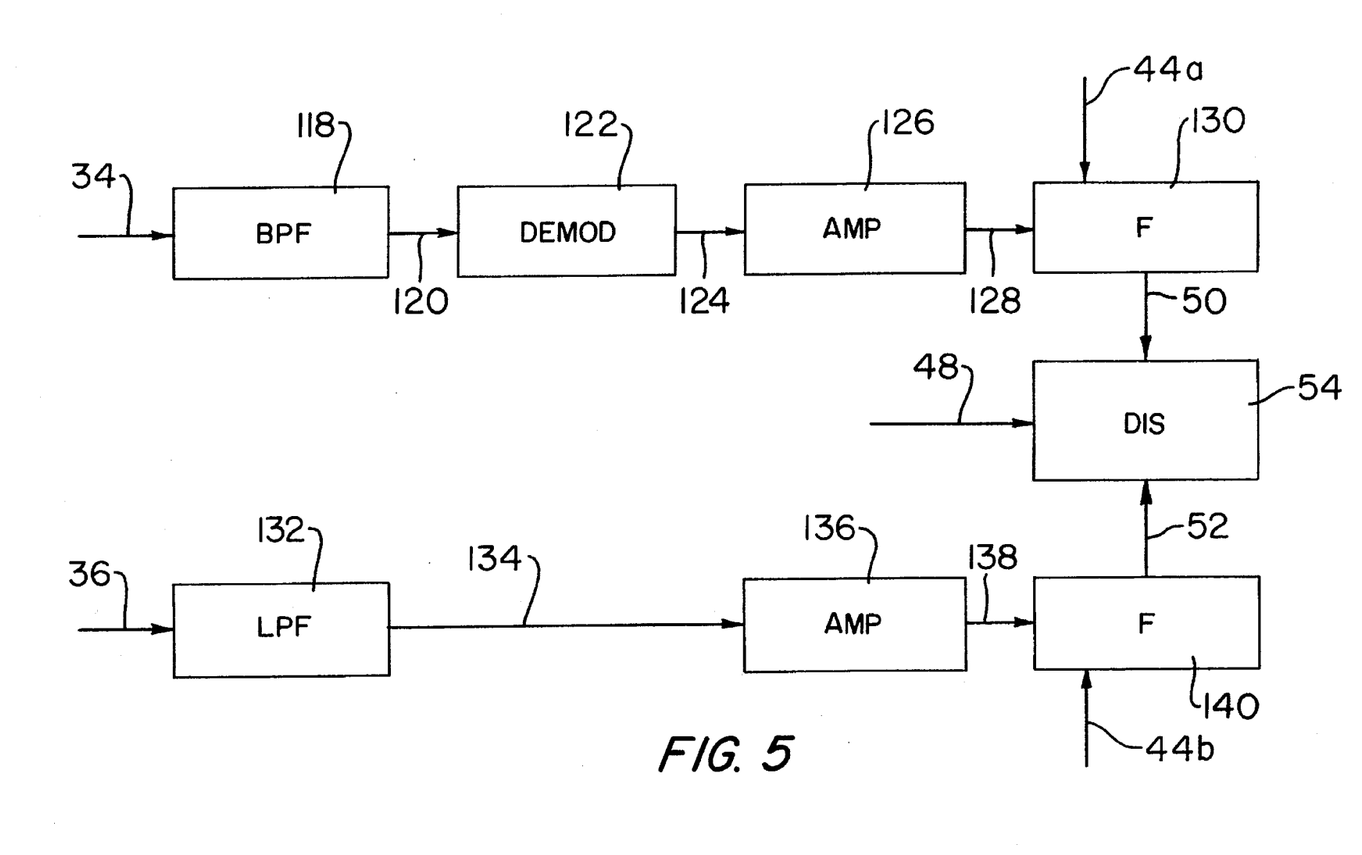
FIG. 5 is a detailed functional block diagram of EC channel 40 and FL channel 42 of the FIG. 1 system, shown with display unit 54.

Referring now to FIG. 5, the line 34 signal is applied to a tuned band pass filter (BPF) 118, which applies the modulated content of the line 34 signal over line 120 to demodulator (DEMOD) 122. The demodulated, rotating speed-related conditional signal is applied over line 124 to amplifier (AMP) 126 and the output signal of amplifier 126 is conducted over line 128 to speed-sensitive band pass filter (F) 130 and, as filtered therein, over line 50 to display 54. Filter 130 receives the FIG. 1 line 44a rotating speed indicative signal and is responsive thereto to set its filtering characteristics for the speed indication at hand.

The line 36 signal is a second input to the signal processing unit of the invention and is applied to a low pass filter (LPF) 132, which blocks high frequency modulated eddy current signals and applies the flux leakage signal over line 134 to amplifier (AMP) 136 and the output signal of amplifier 136 is conducted over line 138 to speed-sensitive band pass filter (F) 140 and, as filtered therein, over line 52 to display 54. Filter 140 receives the FIG. 1 line 44b rotating speed indicative signal and is responsive thereto to set its filtering characteristics for the speed indication at hand.

Display 54 may be comprised of a single channel CRT (cathode ray tube) with chopped input for the display of plural channel information or may comprise a dual channel CRT which has first and second display channels for respective receipt, as display channel inputs, of the signals on lines 50 and 52.

In the system described above, the eddy current channel provides, on its output line 50, indications of mainly top surface conditions, whereas, the flux leakage channel provides, on its output line 52, indications of both top and back surface conditions. Applicants accordingly visually combine both channels to discriminate between top surface and back surface conditions, as below discussed in connection with the illustrative display of FIG. 6.

Figure 6:
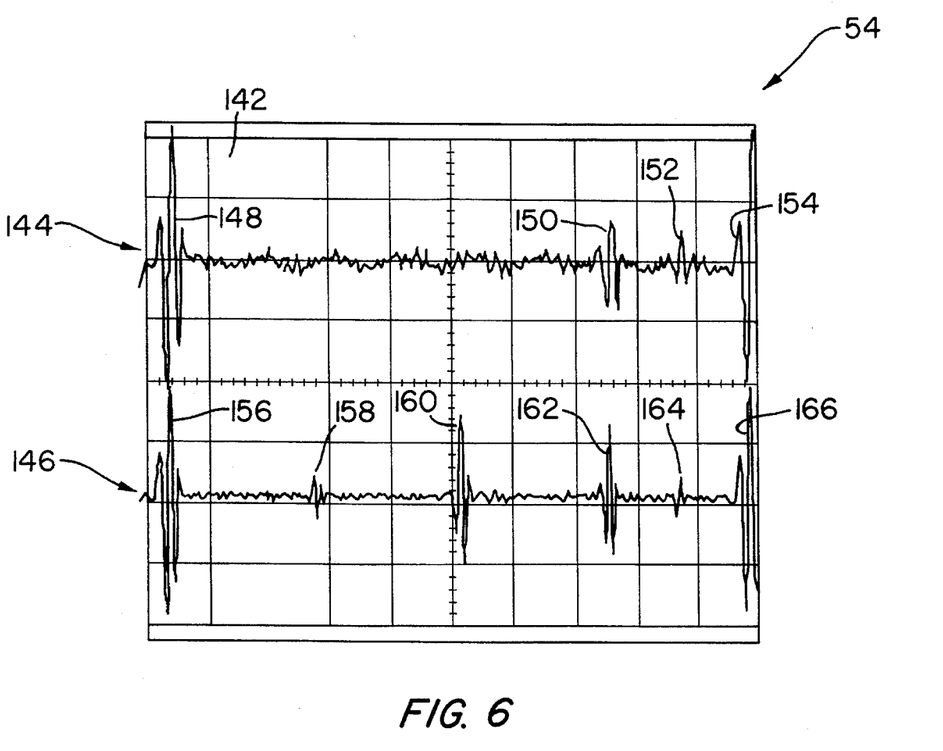
FIG. 6 is a visualization of a display obtainable in accordance with the invention.

Referring to FIG. 6, display 54 is indicated as the screen 142 of a dual channel CRT. The eddy current detected output of the system of FIG. 5 on line 50 thereof is displayed as trace 144 in FIG. 6. The flux leakage detected output of the system of FIG. 5 on line 52 is displayed as trace 146 in FIG. 6. Trace 144 depicts indications of defects at spaced (time-displaced) locations of the tank bottom at 148, 150, 152 and 154. Trace 146 depicts indications of defects at spaced (time-displaced) locations of the tank bottom at 156, 158, 160, 162, 164 and 166. As noted above, the eddy current channel provides, on its output line 50, indications of mainly top surface conditions, whereas, the flux leakage channel provides, on its output line 52, indications of both top and back surface conditions.

In analyzing the FIG. 6 display, one is accordingly provided with the ability to discriminate as between top and back surface tank bottom defects. Thus, since the location probed giving rise to display indications 148 and 156 shows both channels indicating defects, it need be concluded that the defect is a top surface defect. The same need be concluded for locations probed giving rise to display indications 150 and 162, indications 152 and 164 and indications 154 and 166. On the other hand, since the trace 146 indications 158 and 160 do not have counterparts in trace 144, it need be concluded that such indications 158 and 160 result from back surface defects.

The method of the invention thus will be seen to involve the steps of concurrently examining plate structure locations with diverse examination techniques and making a comparison between the detection results of such examination techniques for discriminating as between defects resident in opposed surfaces of the plate structure.

Figure 7:
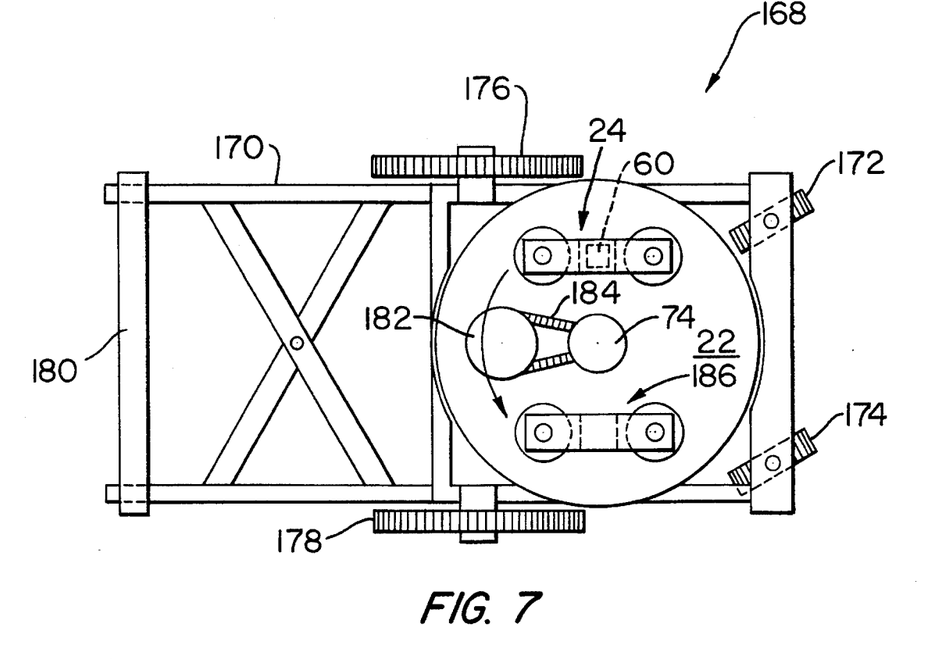
FIG. 7 is a plan view of a mobile test apparatus in accordance with the invention.

Referring to FIG. 7, mobile test apparatus 168 in accordance with the invention is shown in schematic fashion to include a frame 170 supporting front swivel wheels 172 and 174 and frame support wheels 176 and 178. A handle 180 is engageable to move apparatus 168. Rotation platform 22 supports probe apparatus 24 of FIGS. 2 and 3 and permits undersurface 60a of probe 60 (FIG. 2) to be in contiguous engagement with the specimen to be evaluated through movement of probe 60 through platform aperture 22b (FIG. 2). In this connection, eddy current response is sensitive to "lift-off", i.e., the distance between probe 60 and the specimen plate under evaluation. Such distance can vary in the absence of structure providing for the probe to ride directly on the surface of the plate. Accordingly, undersurface 60a is adapted to function as a specimen surface rider, whereby the probe rides in close proximity to the specimen top surface during evaluation. Surface 60a not only keeps a constant probe means lift-off benefitting eddy current response, but improves sensitivity to flux leakage signals for smaller size defects. In this connection, shaft member 62 is preferably spring-biased to a position recessing probe 60 from the specimen surface and is forcibly displaced in the course of specimen evaluation into proximity with the specimen.

Motor 182 of FIG. 7 is engaged drivingly with a shaft member (not shown) under slip ring unit 74, disposed centrally of platform 22, through drive chain 184 to rotate rotation platform 22. Apparatus 186 is disposed on rotation platform 22 diametrically opposite probe apparatus 24 to balance magnetic forces against the specimen being evaluated and includes electromagnets and pole pieces counterpart to those of probe apparatus 24, excited also through slip ring unit 74.

In use of mobile apparatus 168, it is translated across the specimen to be evaluated, e.g., a tank bottom, and, in the course of such translation of the apparatus, platform 22 is continuously rotated by motor 182. Electromagnet drive current, as well as signals issuing from probe apparatus 24, inclusive of both eddy current and flux leakage information are derived through slip ring unit 74 and are evaluated through the display analysis discussed in connection with FIG. 6.

Various changes in structure to the described systems and apparatus may evidently be introduced without departing from the invention. By way of example, while the invention has been described with the preferred usage of separate coils for respective obtaining of eddy current and flux leakage information, the invention contemplates the use of a common coil structure for obtaining both such types of information. In such alternate embodiment, the single coil structure output is applied to both of lines 34 and 36 of FIGS. 1 and 5, filters 118 and 132, being effective for deriving from such single coil structure output the respective eddy current and flux leakage types of information for channels 40 and 42 of FIG. 1. Further, while the preferred embodiment above described makes use of electromagnets for establishing the magnetic field for flux leakage purposes, the invention alternatively contemplates the use of permanent magnets for such purpose. Accordingly, it is to be understood that the particularly disclosed and depicted embodiments and practices are intended in an illustrative and not in a limiting sense. The true spirit and scope of the invention is set forth in the following claims.

What is claimed is:

1. Apparatus for non-destructive examination of a plate for defects existing in one or both of opposed first and second surfaces thereof, said apparatuse comprising:

(a) a platform supported for rotation relative to said plate about a center of said platform;

(b) an eddy current coil structure for inducing eddy currents in said plate located at a first location in said platform remotely of said center thereof;

(c) a magnetic flux leakage detecting coil structure located at said first location in said platform;

(d) first magnetic flux generating means disposed at said first location in said platform;

(e) second magnetic flux generating means disposed at a second location in said platform, said second location being diametrically opposite said first location and remote from said platform center;

(f) drive means for rotating said platform relative to said plate;

(g) signal processing means connected to said eddy current coil structure and to said magnetic flux leakage detecting coil structure and providing output signals indicative of characteristics of said induced eddy currents and characteristics of magnetic flux in said plate; and (h) display means for display of said output signals of said signal processing means.

2. The apparatus claimed in claim 1 wherein said first magnetic flux generating means includes an electromagnet comprised of oppositely excited coils and a pole piece for each coil and wherein said second magnetic flux generating means includes an electromagnet comprised of oppositely excited coils and a pole piece for each coil.

3. The apparatus claimed in claim 2 wherein said eddy current coil structure includes a pair of coils connected in differential manner.

4. The apparatus claimed in claim 3 wherein said magnetic flux leakage detecting coil structure includes a single coil, said single coil and said pair of coils being supported between the pole pieces of said first magnetic flux generating means.

5. The apparatus claimed in claim 4 wherein said single coil is a high permeability cored coil and wherein said pair of coils are air cored.

6. The apparatus claimed in claim 1 wherein said first magnetic flux generating means includes an electromagnet comprised of first and second oppositely excited coils each having a high permeability core and a pole piece connected to said core.

7. The apparatus claimed in claim 1 further including mobile apparatus supporting said platform and said drive means for translation relative to said plate.

\* \* \* \* \*

UNITED STATES PATENT AND TRADEMARK OFFICE
CERTIFICATE OF CORRECTION

PATENT NO. : 5,473,247

DATED : December 5, 1995

INVENTOR(S) : Zhongging You, Robert A. Brooks, Richard Colman and Paul J. Bebick It is certified that error appears in the above-identified patent and that said Letters Patent is hereby corrected as shown below:

In the Abstract, Item [57]:

Line 5, after "platform" insert -- remotely of a center thereof --.

Line 5, after "a" insert -- magnetic flux leakage detecting coil structure located at a first location in the platform a --.

Line 6, after "at" insert --the first location and a second magnetic flux generator disposed at--.

Col. 7, line 36, change "apparatuse" to --apparatus--.

Signed and Sealed this

Twenty-seventh Day of August, 1996

Attest:

BRUCE LEHMAN

Attesting Officer

Commissioner of Patents and Trademarks